United States Patent [19]

Gold et al.

[11] 4,344,755

[45] Aug. 17, 1982

[54] DENTAL HANDPIECE GUIDE

[76] Inventors: Henry O. Gold, 1250 Willow Rd., Winnetka, Ill. 60093; Charles D. Gold, 673 W. Wrightwood Ave., Chicago, Ill. 60614

[21] Appl. No.: 187,084

[22] Filed: Sep. 15, 1980

[51] Int. Cl.³ .............................................. A61C 3/02
[52] U.S. Cl. ...................................................... 433/76
[58] Field of Search ..................... 433/76, 75, 72, 44; 128/136

[56] References Cited

U.S. PATENT DOCUMENTS

| | | | |
|---|---|---|---|
| 2,299,151 | 10/1942 | Kestler | 433/76 |
| 2,695,451 | 11/1954 | Hipp | 433/44 |
| 3,063,149 | 11/1962 | Suga | 433/76 |
| 3,078,580 | 2/1963 | Galvez | 433/76 |
| 3,100,344 | 8/1963 | Sharp | 433/76 |
| 3,254,413 | 6/1966 | Suga | 433/76 |
| 3,380,163 | 4/1968 | Westerman | 433/76 |
| 3,864,832 | 2/1975 | Carlson | 128/136 |

FOREIGN PATENT DOCUMENTS

| | | | |
|---|---|---|---|
| 680764 | 9/1939 | Fed. Rep. of Germany | 433/76 |
| 836993 | 4/1952 | Fed. Rep. of Germany | 433/76 |

Primary Examiner—Gene Mancene
Assistant Examiner—John J. Wilson
Attorney, Agent, or Firm—Dressler, Goldsmith, Shore, Sutker & Milnamow, Ltd.

[57] ABSTRACT

A dental handpiece guide is provided comprising a mounting plate to be secured to the teeth, a moveable adjustment section secured detachably by a suitable fastener to the plate, and a parallel link assembly rotatably mounted on the adjustment section. The parallel link assembly is comprised of at least one set of parallel arms or links. A post carrier assembly pivotally mounted to the distal ends of the parallel arms of the parallel link assembly. A post is pivotally mounted on said post carrier assembly. A sleeve slidingly receives the post and has a projecting arm extending therefrom. The projecting arm has an aperture which receives the head of a dental handpiece. The post can be adjusted to assume a desired orientation relative to the parallel planes containing the parallel link assembly and the post carrier assembly, so that the cutting axis of the dental handpiece cutting instrument can thereby achieve any one of a variety of fixed orientations with respect to the teeth.

11 Claims, 8 Drawing Figures

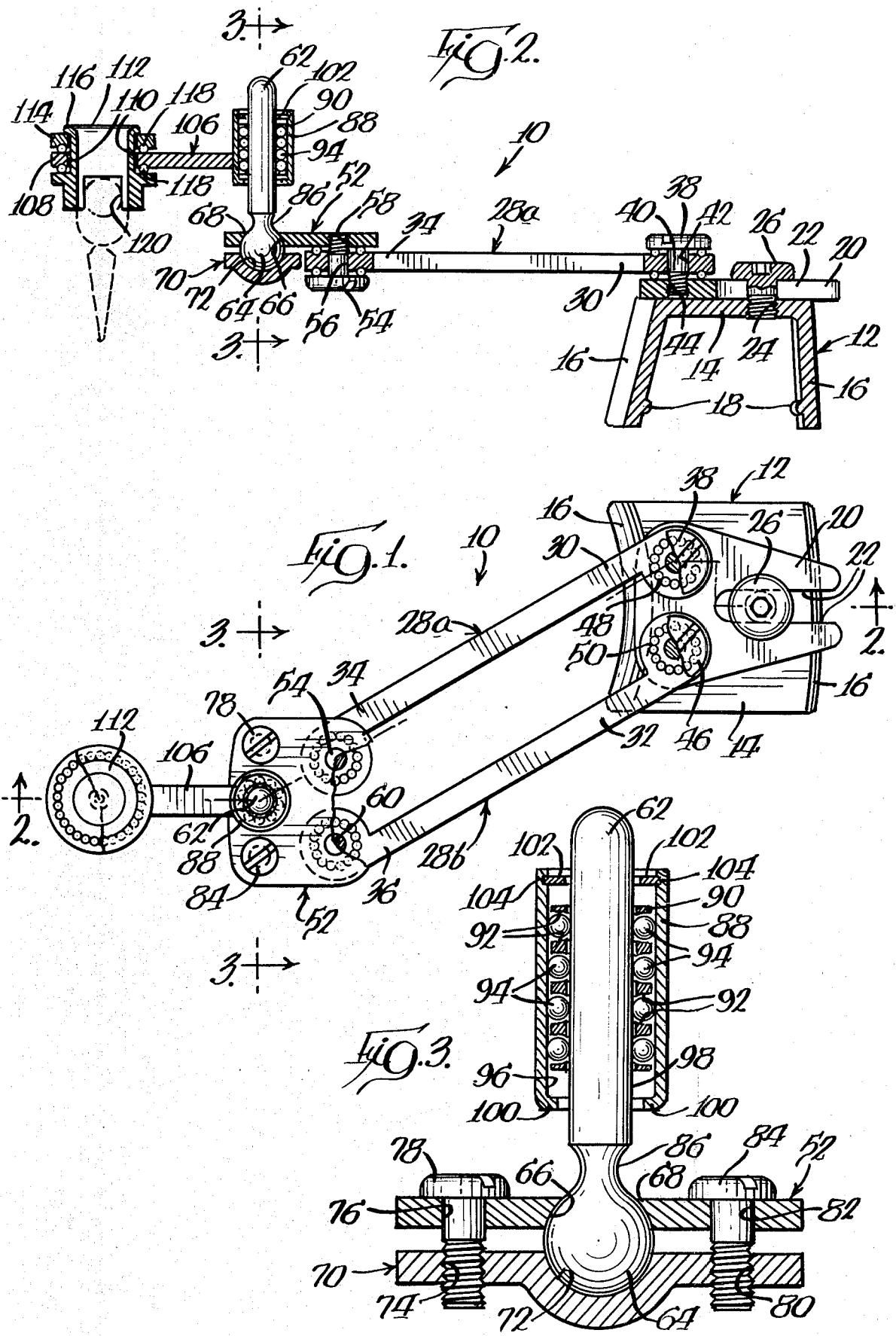

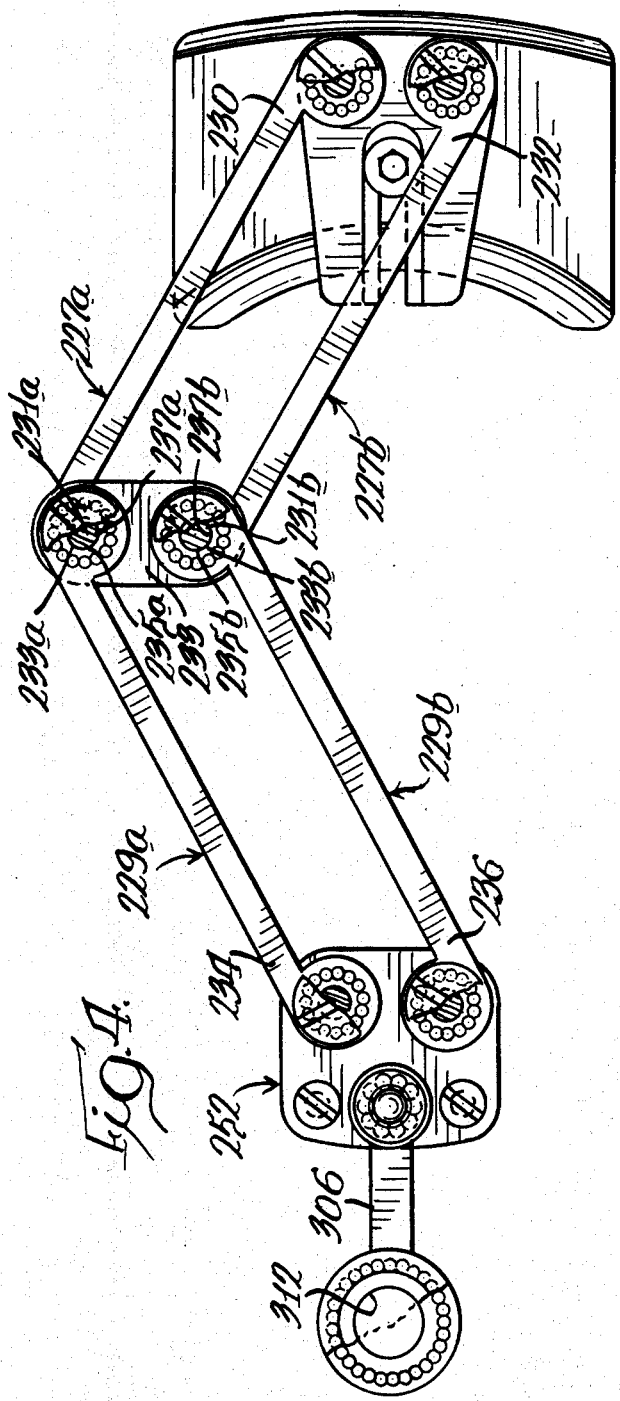

DENTAL HANDPIECE GUIDE

TECHNICAL FIELD OF THE INVENTION

The present invention relates to dental instruments and more particularly to one that functions to guide a dental handpiece cutting instrument.

BACKGROUND OF THE INVENTION

When preparing a person's teeth for installation of a bridge, crown, inlay or pin restoration, it is often necessary to drill parallel holes and/or grind parallel surfaces on the axial surfaces of the patient's teeth. The handpiece guides presently available for such operations are generally bulky, cumbersome, inaccurate and are impractical. Moreover, most prior guides have lacked the desired maneuverability and versatility which is necessary if the dentist is to prepare the teeth with controlled parallelism and taper and a minimum expenditure of time and effort.

Prior art devices have required a massive array of interconnecting arms and pivot members and are thus complicated in design and cumbersome in operation to the point of impracticality.

Typically, the devices have a mounting plate which is to be affixed to the teeth laterally disposed from the tooth to be operated on, or a base plate cast from acrylic or other material and positioned in the mouth. At least two prior art devices have provided for pivotal adjustment of the cutting axis relative to the mounting plate, but such adjustment devices do not provide for easy and relatively acute angle pivotal adjustment of the cutting axis relative to the mounting plate.

Further, some of the prior art devices have not provided for an adequate means to firmly hold a handpiece head to keep the cutting axis from shifting once the desired orientation of the cutting axis is achieved.

Still further, the prior art devices have failed to provide for freedom of rotation and essential vertical movement of an instrument when an operator places unwanted, but unavoidable, lateral or rotational forces on the guide while directing the handpiece in the preparation of teeth.

Still another disadvantage of the prior art devices has been that they have not provided a means to easily and simply disassemble part of the device for removal from the patient's mouth so that the remaining portion of the device retained in the patient's mouth is kept to a minimum and is relatively small in size so that the patient can partially close his jaw to rinse, speak etc. and allow for off-axial preparation of the teeth without disturbing the anchorage of the instrument.

SUMMARY OF THE INVENTION

The foregoing disadvantages of the prior art devices are overcome by the present invention wherein full accessibility, mobility and accuracy of dental operation can be achieved with only a small number of parts compared to the prior devices.

The dental guide of the present invention comprises a base portion having an upper face, and adapted to be secured to the teeth by means of dental silicone or other impression type material. Pivotally and rotatably mounted to the base portion is a parallel link assembly comprising at least two generally parallel arms, mounted at first mounting points so that the link assembly extends from said base portion and lies in a plane generally parallel to the plane containing the upper face. A post carrier assembly is rotatably mounted on the distal ends of said parallel link assembly arms at second mounting points. The second mounting points are spaced from each other generally the same distance as the first mounting points are spaced from each other. A post is mounted on the post carrier assembly and slidably receives a sleeve adapted to rotate about the post. A projecting arm is mounted at one end to the sleeve and has means, at the distal end of said projecting arm, for receiving a dental handpiece so that the central cutting axis of the cutting instrument of the dental handpiece is parallel to the central axis of the sleeve.

Alternatively, an adjustment section is mounted on the base portion and the parallel arms are pivotally mounted on the adjustment section. The adjustment section preferably comprises a plate having a slot extending along one side of the adjustment section which receives a fastener associated with the base portion. The adjustment section is slidingly and removably mounted to the surface area of the base portion so that the distance and direction that the distal ends of the parallel arms extend from the base portion can be adjusted by varying the position of the fastener in the slot. In this way, mounting means, slide means and means for removably mounting the adjustment section to the base portion are provided.

The instrument also has means to permit pivoting of the post relative to the post carrier assembly, and releasable fastener means associated with the pivoting means for fixing the orientation of the axis of the post relative to the post carrier assembly when a desired pivotal orientation is achieved. Thus, when the fastening means fixes the orientation of the post, the axis of the cutting instrument is kept at a fixed orientation with respect to the parallel planes containing the post carrier assembly, the pair of parallel arms, the adjustment section and the base portion.

Full orientation of the cutting instrument axis can be achieved with a minimum of parts and a minimum of rotational axes. The use of a parallel linkage assembly in combination with the pivoting post provides adjustment latitude with freedom of movement while maintaining accuracy of the cutting instrument axis parallelism in a compact mechanism for practical use intraorally to an extent not found in the prior art devices.

The guide thus provides for the cutting instrument axis to be able to move through a cylindrical surface of revolution assuring accurate parallel alignment of said cutting instrument. This mechanism facilitates parallel drilling or grinding with a minimum of parts and simplicity of operation not found in the prior art handpiece guides.

Numerous other advantages and features of the present invention will become readily apparent from the following detailed description of the invention and of embodiments thereof, from the claims and from the accompanying drawing.

BRIEF DESCRIPTION OF THE DRAWING

In the accompanying drawing,

FIG. 1 is a plan view of a first embodiment of a dental handpiece guide shown in partial cross section;

FIG. 2 is a sectional side view of the handpiece guide of the first embodiment taken substantially along line 2—2 of FIG. 1 and looking in the direction of the arrows;

FIG. 3 is an enlarged cross-sectional view taken substantially along line 3—3 of FIG. 2 and looking in the direction of the arrows;

FIG. 4 is a plan view of a second embodiment of the dental handpiece guide shown in partial cross section;

FIG. 5 is a plan view of an alternative base mounting plate and parallel link assembly arrangement;

FIG. 6 is a side view of an alternative arrangement for mounting the projecting arm to the sleeve and a modification of the projecting arm;

FIG. 7 is a plan view of an occlusal clearance guide; and

FIG. 8 is a side view of the occlusal clearance guide.

DESCRIPTION OF THE PREFERRED EMBODIMENTS

In the following description, two digit numerals and three digit numerals in the one hundred series are used to refer to the embodiment illustrated in FIGS. 1, 2 and 3, and three digit numerals in the two hundred and three hundred series are used to refer to the embodiment illustrated in FIG. 4. Other variations of these first two embodiments are illustrated in FIGS. 5, 6, 7 and 8 and are referenced by numerals in the five, six, seven and eight hundred series respectively. The same last two digits in each numeral may, but not necessarily designate similar or functionally analagous elements in the various embodiments. For reference numerals in the one hundred series in FIGS. 1, 2 and 3, similar or functionally analagous elements may be designated by reference numerals in the three hundred series in FIG. 4.

Referring to the drawing FIGS. 1 and 2, the first embodiment of a dental handpiece guide 10 comprises a base portion 12 adapted to be secured to the teeth by means of dental plaster or silicone or the like or other dental impression type material. The base portion 12 preferably comprises a generally planar flat top portion 14 having a planar upper face and lower face and two generally normally extending side plates 16 on opposite sides of the top portion 14. The top upper face of top portion 14 lies in a first defined plane generally parallel to the occlusal planar surface of the teeth and generally normal to the longitudinal axes of the teeth when secured to the teeth.

Each side plate 16 has an undercut means for retaining dental impression type material when said material is received in the region between the two side plates. Shown is one form of such an undercut means in the form of a raised rib 18 disposed inwardly from each side plate substantially along the entire length of the side plate so that when dental silicone plaster or other like impression type material is received in the region between the two side plates, the ribs aid in retention of the dental handpiece guide to the attaching material and to the teeth which are received in the channel formed by the lower face of top portion 14 and side plates 16. The undercut means can take other forms, such as projections or holes defined by the side plates.

Detachably mounted on the upper face of the base portion 14 covering generally the occlusal surface of the teeth is an adjustment section 20. To achieve this detachable mounting, the adjustment section 20 is in the form of a plate having an elongated slot 22 extending along one side of the adjustment section 20 and is aligned with a circular threaded aperture 24 in base portion 14. A suitable releasable fastening means 26 associated with the base portion holds the adjustment section to the base portion by means of a shaft which passes through the slot 22 and aperture 24, when aligned, and is threadably secured in aperture 24. This fastener 26 allows the adjustment section to be slidably and rotatably adjusted, or entirely detached or removed, and provides a means for securing the adjustment section in any desired orientation.

Pivotally mounted to the adjustment section 20 is a parallel link assembly comprising a set of parallel arms or links 28a and 28b, each having near ends 30 and 32, and distal ends 34 and 36, respectively. Alternatively, the parallel link assembly could be mounted directly on the base portion 12, thereby dispensing with an adjustment section 20. Fastener 38 has a threaded shaft 40 which passes through an aperture 42 of the near end 30 of the parallel arm 28a and into a threaded aperture 44 of the adjustment section 20 when the apertures are aligned. Likewise, fastener 46 has a threaded shaft which passes through a similar aperture in the near end 32 of the other parallel arm 28b and into a threaded aperture in the adjustment section 20. The fasteners 38 and 46 holding arms 28a and 28b to adjustment section 20 and base portion 14 define near end or first mounting points. Both near ends 30 and 32 have ball bearing races 48 and 50 which permit the parallel arms 28a and 28b to pivotally rotate relative to the adjustment section 20 in a plane generally parallel to a first defined plane defined by the upper face of top portion 14.

Instead of screw type fasteners, all of the fasteners associated with the ends of the parallel arms could be rivets with ends which may or may not be countersunk and/or flush with the members which they connect.

Pivotally mounted to the distal ends 34 and 36 of the set of parallel arms 28a and 28b is a post carrier assembly 52. Fastener 54 has a shaft which passes through aperture 56 of the distal end 34 of the parallel arm 28a and into threaded aperture 58 of post carrier assembly 52, and has ball bearing races which permit the post carrier assembly 52 to pivotally rotate relative to the parallel arm 28a in a plane generally parallel to the first defined plane. Likewise, fastener 60 has a shaft which passes through a similar aperture in the distal end 36 of the parallel arm 28b and into a threaded aperture (or non-threaded if a rivet is used) in the post carrier assembly 52. The fasteners 54 and 60 holding the post carrier assembly 52 to the arms 28a and 28b define distal end or second mounting points. Both distal ends 34 and 36 have ball bearing races which permit the post carrier assembly to freely rotate relative to the parallel arms 28a and 28b about the shafts of fasteners 54 and 68 in a plane generally parallel to the first defined plane.

The spacing distance between the central axes of fasteners 38 and 46, i.e. the spacing distance between the near end or first mounting points, is generally the same as the spacing distance between the central axes of fasteners 54 and 60, i.e. the spacing distance between the distal end or second mounting points. Thus, the arms 28a and 28b function as a parallel linkage and maintain the central axes of fasteners 38 and 46 of the adjustment section 20 in a parallel position to the central axes of fasteners 54 and 60 of the post carrier assembly 52 throughout the pivotal range of movement of the rotatable parts.

A post 62 is pivotally mounted to the post carrier assembly 52 by means of a ball and socket arrangement. This arrangement comprises a generally spherically shaped ball 64 which is partially received in a first segmented spherical recess 66 defined by the post carrier assembly 52. The post carrier assembly 52 also defines an aperture 68 through which the post 62 projects. The size of the aperture 68 permits it to freely receive the shaft of post 62 but retains from passage therethrough the spherically shaped ball 64.

Also associated with post 62 and post carrier assembly 52 is a releasable fastening means for fixing the orientation of the axis of the post relative to the post carrier assembly 52 when a desired pivotal orientation of the post 62 is achieved relative to the first defined plane. The releasable fastening means comprises a generally rectangular clamping member 70 provided with a second segmented spherical recess 72 which like first recess 66, also partially receives spherically shaped ball 64. The surface of the first and/or second recess may or may not be knurled in order to facilitate the clamping function. The radius of curvature of the segmented spherical recesses 66 and 72 is about the same as the radius of the ball 64, and thus allows for a large amount of surface contact of the rotating clamping member 70 and post carrier assembly 52 with the ball 64 when the fastening means is tightened, as will be described below. While the clamping member 70 has been illustrated as having a rectangular shape, this member can take other shapes capable of performing the same function. For example, the ball can be retained in place by holding means of various shapes, to be held down by one or more fasteners, as will become evident to those skilled in the art to which this apparatus pertains.

To enable the fastening means to be tightened, the clamping member 70 has a pair of threaded bores 74 and 76 positioned on opposing sides of the said segmented spherical recesses 66 and 72 which threadedly receive the ends of a pair of threaded screws or fasteners 78 and 80 after the screws 78 and 80, respectively, pass through bores 82 and 84, respectively, in said post carrier assembly 52. Clamping member 70 is configured so that when first segmented spherical recess 66 and second segmented spherical recess 72 are aligned, threaded bore 74 and bore 76 are also aligned with each other and receive a threaded screw 78. Also, threaded bore 80 and bore 82 are also aligned with each other and receive a threaded screw 84. When threaded screws 78 and 84 are tightened, and the screws are threadedly received by clamping member 70, clamping member 70 will move closer to the post carrier assembly 52 and will prevent the ball 64 from movement within the two segmented spherical recesses 66 and 72, and thereby prevent movement of the post 62 relative to said post carrier assembly 52 and the first defined plane.

Near the lower end of post 62 is a cut away annular channel portion 86 which allows post 62 great pivotal maneuverability with respect to the post carrier assembly 52, and thus a great variety of orientations of the axis of the post 50 can be achieved, while still providing a large amount of surface contact of clamping member 70 and post carrier assembly 52 will ball 64.

The present invention has a novel sleeve and post arrangement which allows the drill to move vertically and pivot about an axis defined by the central axis of the post. This arrangement comprises a generally cylindrically shaped sleeve 88 which is slidably and removably mounted on post 62. Captively received in the hollow portion of the sleeve is a cylinder 90 which is free to rotate therein. As shown in the drawing, the longitudinal length of the cylinder 90 is significantly less than the longitudinal length of the sleeve 88, so that the cylinder is also free to move along its axis and slide within the sleeve 88. When the cylinder 90 receives the post 62 through its hollowed out portion, it is also free to rotate and slide with respect to the post 62. This post, sleeve and cylinder arrangement allows the drill to easily move both vertically and rotationally with respect to the post.

To further enable this vertical and rotational movement, a novel ball bearing arrangement is provided. As best shown in FIG. 3, cylinder 90 has a plurality of segmental spherical recesses 92 defined in its cylinder wall. Each of the segmental spherical recesses 92 receives a spherical ball bearing 94, such that the ball bearing contacts both the interior surface 96 of the sleeve 88 and the exterior surface 98 of the post 62 when the post is received by the cylinder. This ball bearing arrangement more easily enables the cylinder 90 and post 62 to rotate and slide within said sleeve 88.

The cylinder 90 is held captive within the sleeve 88 by means of an annular flange 100 integral with the sleeve 88 and an annular ring 102 which is fitted into annular recess 104 in sleeve 88 after cylinder 90 is received within the sleeve 88.

A ball bushing or linear bearing can be used instead of the assembly depicted in FIG. 3.

A projecting arm 106 is mounted to the exterior of the sleeve 88 at its near end and, as will be described below, provides a means for receiving a dental handpiece. The distal end 108 of the projecting arm defines a generally circular aperture 110 which receives a generally cylindrical basket 112. A generally circular ring 114 encircles the exterior of the basket 112 and is held in place by a flange 116 which is formed on the top of the basket 112 during manufacture, after the circular ring 114 is in place. To more easily enable the basket 112 to rotate within the aperture 110 of projecting arm 106, ball bearing races 118 are provided and disposed between the projecting arm 106 and basket 112 and between the projecting arm 106 and circular ring 114.

Preferably, the basket 112 has its central axis lying along the same line containing the central axis of the aperture 110 defined by the projecting arm. Also, the central axis of the basket 112 is parallel to the central axis of the sleeve 88, cylinder 90, and post 62. Thus, the orientation of the axis of the post 62 relative to the first defined plane can be adjusted, and by tightening the fastening means, one is assured that the axis of the cutting instrument will be parallel to the axis of the post.

The basket is adapted to firmly receive the head of a dental handpiece, illustrated by the dotted lines in FIG. 2, so that when the head of the dental handpiece is completely received by the basket, the central axis of the cutting instrument or other dental attachment is along the same line as the central axis of the basket 112 and will not deviate therefrom. The handpiece is maintained in position in the basket by the application of a temporary type dental cement, silicone or the like. It can thus be readily removed.

It should be understood that any equivalent structure for the projecting arm could be used, i.e. the means for receiving the cutting instrument could receive the cutting instrument either directly or indirectly through a dental handpiece or turbine.

It should be understood that when reference is made to a dental cutting instrument, that this is meant to be a generic term for all dental instruments inserted into a dental handpiece which drill, cut, polish or similarly operate upon a tooth or model thereof.

Basket 112 has, by way of example only, a U-shaped hollowed-out portion 120 defined by its wall to receive the handle of a dental handpiece. This U-shaped hollowed-out portion defined by the basket's wall allows for the basket to seat fully over the handle of the handpiece.

Referring now to FIG. 4, a second embodiment of a handpiece guide will now be described. The embodiment has a parallel link assembly comprising two sets of parallel arms or links, instead of one set as with the previously described embodiment. The first set of generally parallel arms 227a and 227b have near ends 230 and 232. The second set of generally parallel arms 229a and 229b have distal ends 234 and 236, respectively. The near ends 230 and 232 of parallel arms 227a and 227b could be mounted in any one of the various ways described above for the first embodiment, i.e. directly to the base portion, or to an adjustment section. The distal ends 234 and 236 of the second set of parallel arms are analagous in function to the distal ends 34 and 36 of the set of parallel arms in the first embodiment.

Thus, the parallel link assembly in the first embodiment comprises one set of parallel arms, whereas in the second embodiment the parallel link assembly comprises two sets of parallel arms. In the second embodiment, the first and second set of parallel arms are joined at intermediary points 231a and 231b on an intermediary member 233. The intermediary member has a pair of apertures 233a and 233b to receive suitable fasteners which pass through the apertured ends 235a and 235b of the first set of arms, and the apertured first ends 237a and 237b of the second set of arms. The apertured ends 235a and 235b in the first set of arms 227a and 227b are at ends opposite from the near ends 230 and 232, respectively. Similarly, the apertured first ends 237a and 237b in the second set of arms 229a and 229b are at ends opposite from distal ends 234 and 236, respectively.

Thus, whereas in the first embodiment the near ends and distal ends of the parallel link assembly are on one set of arms or links, in the second embodiment the near ends are on the first set of links and the distal ends are on the second set of links.

The distance between the intermediary mounting points 231a and 231b is generally the same as the distance that the near end or first mounting points are from each other. Also, this distance is the same distance as the distance that the distal end or second mounting points are from each other. In this way complete parallelism of the parallel link assembly is maintained. As will be appreciated the second embodiment has 2 parallelograms formed by its parallel link assembly, whereas the first embodiment has one parallelogram. In other respects, the two embodiments are virtually identical.

Referring now to FIG. 5, an alternative arrangement for mounting the parallel link assembly to the base portion 14 will now be described. Such an arrangement comprises two tubes 525 and 527 rotatably mounted on the base portion at first mounting points. Each tube slidingly receives therein the near ends 30 and 32 of the parallel arms 28a and 28b. Of course, the parallel link assembly of the second embodiment could also be used with this mounting arrangement. The near ends 30 and 32 have stop means in the form of enlarged ends which prevent escape of the arms from the tubes. A releasable locking means is provided for preventing movement of said arms in said tubes when the position of the arms within the tubes is achieved. This locking means could be in the form of a releasable spring clamp, or as shown, by a pair of fasteners 529.

Referring now to FIG. 6 an alternative arrangement is shown for mounting the projecting arm 106 to the sleeve 688 so as to permit relative adjustment therebetween. This is facilitated by means of providing a releasable clamp 609 associated with the projecting arm 106 which encircles the sleeve 688. A suitable releasable fastener can fix the relative position of the projecting arm and sleeve. Such relative adjustment may be desired to enable an operator to have a larger range of movement and thus more accessibility while still maintaining the orientation of the axis of the dental instrument relative to the point where the handpiece guide is mounted to the dental arch.

Also, the projecting arm is shown alternatively comprised of two sections so that one section slides within the other in a telescopic arrangement. Thus, the length of the projecting arm can be adjusted if needed. Releasable clamping means can be provided to fix the relative position of the sections once the overall desired length of the projecting arm is achieved.

Referring now to FIGS. 7 and 8, an occlusal clearance guide for use in combination with the dental handpiece guide will now be described. This clearance guide is designed especially when initially fitting the base portion 14 onto the dental arch with dental attachment or impression material. As noted, the adjustment section 20 is capable of being detached from the base portion 14. When so detached, the base portion 14 can receive the clearance guide 701 which has an elongated slot 722 similar in configuration to the elongated slot 22 of the adjustment section. When the clearance guide 701 is so situated on the base portion 14, the flat surface of outer portion 723 should be rested and held against the occlusal surface of the opposite side of the dental arch while the dental attachment or impression material is setting. The clearance guide is configured so that when the flat surface of outer portion 723 is held against the opposite side of the arch when the dental attachment or impression material is setting, removal of the clearance guide 701 and replacement thereof by the adjustment section and remainder of the handpiece guide after the dental attachment or impression material has set will result in the post carrier assembly just clearing the occlusal plane of the dental arch, and will result in maximum accessibility of a dental instrument placed in the basket.

Thus, with the present invention, greater mobility of a drilling device is achieved with a compact guide having only a small number of parts, and compactness and complexity of the guide is substantially reduced over prior art devices, while still offering full accessibility of a drill to all coordinates within its range.

Further, since the means to permit pivoting the cutting instrument's central axis relative to the first plane is located at the nearest effective rotational axis from the cutting axis, a more precise adjustment of the pivot can be obtained than with prior art devices where the pivot point is more than one axis of rotation away from the cutting axis. Therefore, whereas in prior art devices a small adjustment in the pivot orientation results in a significant vertical displacement of the drilling or cutting receiving member, in the present invention a corresponding adjustment in the pivot orientation will result in a much smaller vertical displacement of the dental handpiece. Therefore, full mobility with accurate orientation of the cutting or drilling axis may be achieved without large displacements of the components of the dental handpiece which might interfere with the movement of the handpiece or necessitate a patient keeping his or her mouth open an inordinate amount.

Depending upon the location of the tooth or teeth to be operated on, the dental handpiece guide device may be mounted on either the upper or lower left, right, posterior or anterior of the dental arch.

The projecting arm can be easily removed from the post, by merely sliding the sleeve section off of the post without the need for releasing any retaining device. This partial disassembling can allow the dentist to more readily change cutting instruments and allow the patient to rest while the dentist is performing other operations. Further, because the fastener 26 can be released and thus allow the section 20 to be removed, the entire instrument can be removed from the patient's mouth except for the base portion 14 which remains secured by dental silicone or the like. This provides further opportunity for the patient to rest during a dental procedure, while still allowing the instrument to be easily reassembled and accurately realigned.

From the foregoing, it will be observed that numerous variations and modifications may be effected without departing from the true spirit and scope of the novel concept of the invention. It is to be understood that no limitations with respect to the specific apparatus illustrated herein is intended or should be inferred. It is, of course, intended to cover by the appended claims all such modifications as fall within the scope of the claims.

What is claimed is:

1. A dental handpiece guide for guiding a cutting instrument to cut parallel surfaces, cuts or holes in the axial direction on teeth in a mouth or on a model, comprising:

a base portion adapted to be secured to the teeth, said base portion having an upper face;
   a parallel link assembly rotatably mounted on said base portion at first mounting points, and extending from said base portion and lying in a plane generally parallel to the plane containing the upper face, said parallel link assembly comprising at least one set of two generally parallel arms;
   a post carrier assembly rotatably mounted on the distal ends of the arms of said parallel link assembly at second mounting points, said second mounting points being spaced from each other generally the same distance as the first mounting points of said base portion are from each other;
   a post mounted on said post carrier assembly;
   a sleeve slidably received by said post and adapted to rotate about the post; and
   a projecting arm having one end mounted to said sleeve, and having means at the distal end of said projecting arm for receiving a cutting instrument, which comprises a generally circular aperture, and wherein a generally cylindrical basket is received by said projecting arm through its aperture and held from escape by a circular ring and flange on the basket, the central axis of the basket and the central axis of the sleeve are substantially parallel, which basket has a hollowed-out portion defined by its wall to receive the handle of a cutting instrument when a cutting instrument is received by said basket.

2. The dental handpiece guide of claim 1 wherein said basket has ball bearing races so that the basket can more easily rotate within the aperture of the projecting arm.

3. A dental handpiece guide for guiding a cutting instrument to cut parallel surfaces, cuts or holes in the axial direction on teeth in a mouth or on a model, comprising:

a base portion adapted to be secured to the teeth, said base portion having an upper face;
   a parallel link assembly rotatably mounted on said base portion at first mounting points, and extending from said base portion and lying in a plane generally parallel to the plane containing the upper face, said parallel link assembly comprising at least one set of two generally parallel arms;
   a post carrier assembly rotatably mounted on the distal ends of the arms of said parallel link assembly at second mounting points, said second mounting points being spaced from each other generally the same distance as the first mounting points of said base portion are from each other;
   a post mounted on said post carrier assembly;
   a sleeve slidably received by said post and adapted to rotate about the post, said sleeve having a cylinder captively received in a hollow portion defined by the sleeve and is free to rotate within said sleeve, and wherein the length of the cylinder is less than the length of the sleeve, so that the cylinder is able to move freely along its axis within the sleeve; and
   a projecting arm having one end mounted to said sleeve, and having means at the distal end of said projecting arm for receiving a cutting instrument so that the central cutting axis of the cutting instrument is parallel to the central axis of said sleeve.

4. The dental handpiece guide of claim 3 wherein the cylinder defines at least one segmental spherical recess in its wall which can receive a spherical ball bearing, so that the ball bearing contacts the interior surface of the sleeve and the exterior surface of the post when said post is received by said cylinder, to more easily enable the cylinder and post to rotate and slide within said sleeve.

5. A dental handpiece guide for guiding a cutting instrument to cut parallel surfaces, cuts or holes in the axis direction on teeth in a mouth or on a model, comprising:

a base portion adapted to be secured to the teeth, said base portion having an upper face;
   a parallel link assembly rotatably mounted on said base portion at first mounting points, and extending from said base portion and lying in a plane generally parallel to the plane containing the upper face, said parallel link assembly comprising at least one set of two generally parallel arms and two tubes rotatably mounted on said base portion at said first mounting points, each tube slidably receiving therein one of said parallel arms, having stop means for preventing escape of said arms from said tubes and releasable locking means for preventing movement of said arms in said tubes when the position of said arms relative to said tubes is achieved;
   a post carrier assembly rotatably mounted on the distal ends of the arms of said parallel link assembly at second mounting points, said second mounting points being spaced from each other generally the same distance as the first mounting points of said base portion are from each other;
   a post mounted on said post carrier assembly;
   a sleeve slidably received by said post and adapted to rotate about the post; and
   a projecting arm having one end mounted to said sleeve, and having means at the distal end of said projecting arm for receiving a cutting instrument so that the central cutting axis of the cutting instrument is parallel to the central axis of said sleeve.

6. A dental handpiece guide for guiding a cutting instrument to drill parallel cavities or to grind parallel axis surfaces in or on teeth comprising:
   a base portion having a lower face adapted to be secured to the teeth, and a planar upper face;
   a parallel link assembly comprising two generally parallel arms having near ends pivotally mounted to said base portion so that the parallel arms can rotate in a plane generally parallel to the plane containing the upper face;
   a post carrier assembly pivotally mounted to the distal ends of said parallel arms, so that said post carrier assembly can rotate in a plane generally parallel to the plane containing the upper face;
   a post mounted on said post carrier assembly, said instrument having means to permit pivoting of said post relative to said post carrier assembly and having releasable fastening means associated with said pivoting means for fixing the orientation of the axis of the post relative to said post carrier assembly when a desired pivotal orientation of the post is achieved;
   a generally cylindrically shaped sleeve;
   a cylinder captively received in the hollow portion of said sleeve and free to rotate within said sleeve, and wherein the longitudinal cylinder length is less than the longitudinal length of the sleeve, so that the cylinder is free to move along its axis within said sleeve, and where said cylinder receives said post to rotate and slide with respect thereto;
   a projecting arm having one end mounted to the exterior of said sleeve, and having a generally circular aperture defined by its distal end, and wherein a generally cylindrical basket, having an annular groove around its exterior, is received by said projecting arm through its aperture along the groove portion of the basket so that the central axis of the basket and the central axis of the sleeve are essentially parallel and wherein when the basket firmly receives a dental handpiece instrument, its central cutting instrument axis passes through the aperture and is essentially parallel to the central axis of said sleeve.

7. The dental handpiece guide of claim 6 wherein said means to permit pivoting comprises a generally spherically shaped ball at the mounted end of said post and a first segmented spherical recess defined by said post carrier assembly which partially receives said ball, and wherein said post carrier assembly defines an aperture to freely receive said post, but where said spherical ball is retained from passage through said aperture, and wherein said releasable fastening means comprises:
   a clamping member defining a second segmented spherical recess which partially receives the ball;
   a pair of threaded screws;
   a first pair of bores identified by said post carrier assembly to freely receive said screws; and
   a second pair of threaded bores defined by said clamping member which threadedly receive said screws after the screws are first received by said first pair of bores, so that when said ball is received by said second recess and the shaft of said post is received by said post carrier assembly aperture, a tightening of said pair of screws will prevent the movement of the post relative to said post carrier assembly, and a loosening of said pair of screws will permit the post to move and pivot relative to the post carrier assembly.

8. The dental handpiece guide of claim 6 wherein said basket has a U-shaped hollowed-out portion defined by its wall to receive the handle of a dental handpiece when a dental handpiece is received by said basket.

9. The dental handpiece guide of claim 6 wherein said annular groove has ball bearings received therein so that the basket can more easily rotate in the aperture of the projecting arm.

10. The dental handpiece guide of claim 6 wherein the cylinder defines at least one segmented spherical recess in its wall which can receive a spherical ball bearing, whereby the ball bearing contacts the interior surface of the sleeve and the exterior surface of the post when said post is received by said cylinder, to more easily enable the cylinder and post to rotate and slide within said sleeve.

11. A dental handpiece guide for guiding a cutting instrument to drill parallel cavities or to grind parallel axial surfaces in or on teeth comprising:
   a base portion having a lower face adapted to be secured to the teeth, and a planar upper face;
   a parallel link assembly comprising a first set of two generally parallel arms and a second set of two generally parallel arms, said first set having near ends pivotally and rotatably mounted on said base portion at first mounting points, said second set having first ends rotatably mounted at the ends of said first set opposite from said near ends, so that both sets of the parallel arms can rotate in a plane generally parallel to the plane containing the upper face;
   a post carrier assembly pivotally mounted to distal ends of the second set of said parallel arms, so that said post carrier assembly can rotate in a plane generally parallel to the plane containing the upper face;
   a post mounted on said post carrier assembly, said instrument having means to permit pivoting of said post relative to said post carrier assembly and having releasable fastening means associated with said pivoting means for fixing the orientation of the axis of the post relative to said post carrier assembly when a desired pivotal orientation of the post is achieved;
   a generally cylindrically shaped sleeve;
   a cylinder captively received in the hollow portion of said sleeve and free to rotate within said sleeve, and wherein the longitudinal cylinder length is less than the longitudinal length of the sleeve, so that the cylinder is free to move along its axis within said sleeve, and where said cylinder receives said post to rotate and slide with respect thereto;
   a projecting arm having one end mounted to the exterior of said sleeve, and having a generally circular aperture defined by its distal end, and wherein a generally cylindrical basket, having an anular groove around its exterior, is received by said projecting arm through its aperture along the groove portion of the basket so that the central axis of the basket and the central axis of the sleeve are essentially parallel and wherein when the basket firmly receives a dental handpiece so that its central cutting instrument axis passes through the aperture and is essentially parallel to the central axis of said sleeve.

* * * * *